United States Patent
Meves

(10) Patent No.: US 11,060,151 B2
(45) Date of Patent: Jul. 13, 2021

(54) METHODS AND MATERIALS FOR STAGING AND TREATING SKIN CANCER

(71) Applicant: Mayo Foundation for Medical Education and Research, Rochester, MN (US)

(72) Inventor: Alexander Meves, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 93 days.

(21) Appl. No.: 16/099,483

(22) PCT Filed: May 10, 2017

(86) PCT No.: PCT/US2017/031908
§ 371 (c)(1),
(2) Date: Nov. 7, 2018

(87) PCT Pub. No.: WO2017/196944
PCT Pub. Date: Nov. 16, 2017

(65) Prior Publication Data
US 2019/0169694 A1 Jun. 6, 2019

Related U.S. Application Data

(60) Provisional application No. 62/334,302, filed on May 10, 2016.

(51) Int. Cl.
| | | |
|---|---|---|
| C12Q 1/68 | (2018.01) | |
| C07H 21/04 | (2006.01) | |
| C12Q 1/6886 | (2018.01) | |
| G16B 25/00 | (2019.01) | |
| G01N 33/574 | (2006.01) | |
| G16H 50/20 | (2018.01) | |

(52) U.S. Cl.
CPC ....... *C12Q 1/6886* (2013.01); *G01N 33/5743* (2013.01); *G16B 25/00* (2019.02); *G16H 50/20* (2018.01); *C12Q 2600/106* (2013.01); *C12Q 2600/112* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,695,913 B2 | 4/2010 | Cowens et al. |
| 2004/0010045 A1 | 1/2004 | Yi |
| 2004/0110221 A1 | 6/2004 | Twine et al. |
| 2006/0235001 A1 | 10/2006 | Elliott et al. |
| 2007/0154889 A1 | 7/2007 | Wang |
| 2009/0125247 A1 | 5/2009 | Baker et al. |
| 2010/0028876 A1 | 2/2010 | Gordon et al. |
| 2011/0123997 A1 | 5/2011 | Kashani-Sabet et al. |
| 2011/0159496 A1 | 6/2011 | Kashani-Sabet et al. |
| 2012/0071343 A1 | 3/2012 | Ma et al. |
| 2012/0128667 A1 | 5/2012 | Chow et al. |
| 2014/0045915 A1 | 2/2014 | Skog et al. |
| 2015/0290289 A1 | 10/2015 | Sampath |
| 2016/0222457 A1* | 8/2016 | Meves ............ A61P 35/00 |
| 2017/0275700 A1* | 9/2017 | Meves ............ C07K 16/3053 |

FOREIGN PATENT DOCUMENTS

| | | | |
|---|---|---|---|
| WO | 2014/077915 A1 | 5/2014 | |
| WO | 2016/025717 A1 | 2/2016 | |
| WO | WO2016/025717 | * 2/2016 | ............ C12Q 1/68 |
| WO | 2017/196944 | 11/2017 | |

OTHER PUBLICATIONS

Meves et al. (J. of Clinical Oncology, vol. 33, No. 23, pp. 2509-2515. Aug. 10, 2015) (Year: 2016).*
European Search Report and Opinion for European Application No. 17796741, dated Sep. 12, 2019, 7 pages.
King et al. Gene Expression Profile Analysis by DNA Microarrays. JAMA 2001, vol. 286, No. 18, pp. 2280-2288 (Year 2001).
Sun Yang et al. Overabundance of Putative Cancer Stem Cells in Human Skin Keratinocyte Cells Malignantly Transformed by Arsenic. Toxicol Sci, Jan. 2012, 125(1), pp. 20-29. Published online Oct. 19, 2011. doi: 10.1093/toxsci/kfr282, pp. 1-11.
Yoo et al., "A Comparison of Logistic Regression, Logic Regression, Classification Tree, and Random Forests to Identify Effective Gene-Gene and Gene-Environmental Interactions" International journal of applied science and technology, Aug. 2012, vol. 2, No. 7, pp. 268-284, especially abstract, p. 274, last para, p. 275, 3rd para, last para.
Whelan et al., "A method for the absolute quantification of cDNA using real-time PCR," J. Immunol. Methods, 278(1-2):261-9, Jul. 2003.
Warters et al., "Differential gene expression in primary human skin keratinocytes and fibroblasts in response to ionizing radiation," Radiat Res., 172(1):82-95, Jul. 2009.
Waalkes et al., "Pentamidine: clinical pharmacologic correlations in man and mice," Clin Pharmacol Ther., 11(4):505-512, Jul.-Aug. 1970.
Talantov et al., "Novel genes associated with malignant melanoma but not benign melanocytic lesions," Clin Cancer Res., 11(20):7234-7242, Oct. 15, 2005.
Sun et al., "Overabundance of putative cancer stem cells in human skin keratinocyte cells malignantly transformed by arsenic," Toxicol Sci., 125(1):20-29, Epub Oct. 19, 2011.
Sun and Zhang, "Pentamidine binds to tRNA through non-specific hydrophobic interactions and inhibits aminoacylation and translation," Nucleic Acids Res., 36(5):1654-1664, Mar. 2008.
Smith et al., "The effect of pentamidine on melanoma ex vivo," Anticancer Drugs, 21(2):181-185, Feb. 2010.

(Continued)

*Primary Examiner* — Jeanine A Goldberg
(74) *Attorney, Agent, or Firm* — TraskBritt

(57) ABSTRACT

This document provides methods and materials for staging and treating skin cancer (e.g., metastatic malignant pigmented skin lesions). For example, methods and materials for using an ITLP expression profile and/or models including an ITLP expression profile to stage skin cancer and/or determine treatment options for skin cancer patients are provided.

6 Claims, 13 Drawing Sheets

(56) References Cited

OTHER PUBLICATIONS

Simon et al., "Expression of CD44 isoforms in human skin cancer," Eur J Cancer., 32A(8):1394-1400, Jul. 1996.
Siiskonen et al., "Chronic UVR causes increased immunostaining of CD44 and accumulation of hyaluronan in mouse epidermis," J Histochem Cytochem., 59(10):908-917, Epub Aug. 10, 2011.
Seo et al., "The effect of substrate microtopography on focal adhesion maturation and actin organization via the RhoA/ROCK pathway," Biomaterials., 32(36):9568-9575, Epub Sep. 16, 2011.
Sanovic et al., "Time-resolved gene expression profiling of human squamous cell carcinoma cells during the apoptosis process induced by photodynamic treatment with hypericin," Int. J. Oncol., 35(4):921-39, Oct. 2009.
Ruczinski et al., "Logic regression," Journal of Computational and Graphical Statistics, 12(3):475-511, 2003.
Pathak et al., "Pentamidine is an inhibitor of PRL phosphatases with anticancer activity," Mol Cancer Ther., 1(14):1255-1264, Dec. 2002.
NEB catalog (1998/1999), pp. 121, 284. (Year: 1998).
Mitra et al., "Melanoma sentinel node biopsy and prediction models for relapse and overall survival," Br J Cancer., 103(8):1229-1236, Epub Sep. 21, 2010.
Meves et al., "Beta1 integrin cytoplasmic tyrosines promote skin tumorigenesis independent of their phosphorylation," Proc Natl Acad Sci U S A., 108(37):15213-15218, Epub Aug. 29, 2011.
Lee et al., "The novel combination of chlorpromazine and pentamidine exerts synergistic antiproliferative effects through dual mitotic action," Cancer Res., 67(23):11359-11367, Dec. 1, 2007.
Kashani-Sabet et al., "A multi-marker assay to distinguish malignant melanomas from benign nevi," Proc Natl Acad Sci U S A., 106(15):6268-6272, Epub Mar. 30, 2009.
International Search Report and Written Opinion received for PCT Patent Application No. PCT/US2017/031908, dated Aug. 22, 2017, 6 pages.
International Preliminary Report on Patentability received for PCT Patent Application No. PCT/US2017/031908, dated Nov. 22, 2018, 6 pages.
Infante JR et al., "Safety, pharmacokinetic, and pharmacodynamic phase I dose-escalation trial of PF-00562271, an inhibitor of focal adhesion kinase, in advanced solid tumors," J Clin Oncol., 30(13):1527-1533, Epub Mar. 26, 2012.
Hartman et al., "The Evolution of S100B Inhibitors for the Treatment of Malignant Melanoma", Future medicinal chemistry, Jan. 2013, vol. 5, No. 1, pp. 97-109. (available in PMC. Web pp. 1-25), especially abstract, p. 5, 2nd para, p. 7, last para-p. 8, 1st par.
Coppe et al., "Senescence-associated secretory phenotypes reveal cell-nonautonomous functions of oncogenic RAS and the p53 tumor sunnressor," PLoS Biol., 6(12):2853-2868, Dec. 2, 2008.
Conway et al., "Gene expression profiling of paraffin-embedded primary melanoma using the DASL assay identifies increased osteopontin expression as predictive of reduced relapse-free survival," Clin Cancer Res., 15(22):6939-6946, Epub Nov. 3, 2009.
ClinicalTrials.gov Identifier: NCT00729807, "Pentamidine in Treating Patients With Relapsed or Refractory Melanoma," ClinicalTrials. gov [online] 2008 [retrieved on Mar. 26, 2015]. Retrieved from the Internet: <URL: https://www.clinicaltrials.gov/ct2/show/NCT00729807?term=NCT00729807&rank= 1>, 4 pages.
Chan et al., "Regulation of adhesion dynamics by calpain-mediated proteolysis of focal adhesion kinase (FAK)," J Biol Chem., 285(15):11418-11426, Epub Feb. 11, 2010.
Carlson et al., "Establishment, maintenance and in vitro and in vivo applications of primary human glioblastoma multiforme (GBM) xenograft models for translational biology studies and drug discovery," Curr Protoc Pharmacol., Chapter 14:Unit 14.16, Mar. 2011.
Bullard et al., "Evaluation of statistical methods for normalization and differential expression in mRNA-Seq experiments," BMC Bioinformatics 11:94, Feb. 18, 2010.
Breslow, "Thickness, cross-sectional areas and depth of invasion in the prognosis of cutaneous melanoma," Ann Surg., 172(5):902-908, Nov. 1970.
Bernard et al., "Use of a new bioassay to study pentamidine pharmacokinetics," J Infect Dis., 152(4):750-754, Oct. 1985.
Benjamin et al., "p53 and the Pathogenesis of Skin Cancer", Toxicol Appl Pharmacol., Nov. 1, 2007;.vol. 224 No. 3, pp. 241-248 (available in PMC Nov. 1, 2008, pp. 1-13), especially abstract, p. 2, 3rd para, p. 3, 2nd para, p. 4, last para, p. 7, last para-p. 8, 1st para.
Balch et al., "Sentinel node biopsy and standard of care for melanoma," J Am Acad Dermatol., 60(5):872-875, May 2009.
Balch et al., "Final version of 2009 AJCC melanoma staging and classification," J Clin Oncol., 27(36):6199-6206, Epub Nov. 16, 2009.
Anders and Huber, "Differential expression analysis for sequence count data," Genome Biol., 11(10):R106, Epub Oct. 27, 2010.
(Meves, A et al.) Tumor Cell Adhesion As a Risk Factor for Sentinel Lymph Node Metastasis in Primary Cutaneous Melanoma. Journal of Clinical Oncology. Aug. 10, 2015, vol. 33, No. 23; pp. 2509-2515; abstract; p. 2510, 1st column, 3rd paragraph; p. 2511, 2nd column, 4th paragraph; p. 2513, 2nd column, 2nd paragraph; Table 3.
(American Joint Committee on Cancer) AJCC Cancer Staging Manual. Technical Manual [online]. 2002 [Retrieved on Jul. 28, 2017]. Retrieved from the Internet: <URL: https://cancerstaging.org/references-tools/deskreferences/Documents/AJCC6thEdCancerStagingManualPart2.pdf>; p. 209, Summary of Changes.
(Annex 1) American Cancer Society "Treatment of Melanoma Skin Cancer, by Stage" 4 pages, accessed Nov. 19, 2020, https://www.cancer.org/cancer/melanoma-skin-cancer/treating/by-stage.html.

* cited by examiner

Cohorts
Model Development and Validations

| Characteristic | Model development cohort (N=360) | Model validation cohort (N=146) | P value † |
|---|---|---|---|
| Male gender, n (%) | 225 (62.5%) | 101 (69.2%) | 0.16 |
| Age at SLN (years), mean (SD) | 59.6 (17.0) | 63.0 (15.0) | 0.03 |
| Age at SLN (years), n (%) | | | 0.11 |
|   16-39 | 55 (15.3%) | 13 (8.9%) | |
|   40-59 | 112 (31.1%) | 43 (29.5%) | |
|   60+ | 193 (53.6%) | 90 (61.6%) | |
| Breslow depth (mm) | | | 0.41 |
|   0.50-1 | 93 (25.8%) | 35 (25.0%) | |
|   1.01-2 | 177 (49.2%) | 66 (45.2%) | |
|   2.01-4 | 90 (25.0%) | 45 (30.8%) | |
| Ulceration, n (%) | 65 (18.1%) | 24 (16.4%) | 0.66 |
| Mitotic rate, n (%) | | | 0.23 |
|   Absent | 42/346 (12.1%) | 11/132 (8.3%) | |
|   1-6 | 246/346 (71.1%) | 104/132 (78.8%) | |
|   >6 | 58//346 (16.8%) | 17/132 (12.9%) | |
| SLN metastasis, n (%) | 74 (20.6%) | 43 (29.5%) | 0.03 |

IQR, interquartile range; SLN, sentinel lymph node

†Comparisons of the model development and model validation cohort were performed using the chi-square test for categorical variables, the two-sample t-test for patient age, and the Wicoxon rank sum test for all other variables.

FIG. 12

Multivariable Model; SLN+

| Factor | Proportion with SLN metastasis | Clinicopathologic multivariate model | | Clinicopathologic + molecular multivariate model | |
|---|---|---|---|---|---|
| | | Adjusted OR (95% CI) | P value | Adjusted OR (95% CI) | P value |
| Age at SLN (years) | | | <0.001 | | <0.001 |
| 16-39 | 16/55 (29.1) | 3.85 (1.75, 8.50) | | 5.14 (1.99, 13.25) | |
| 40-59 | 33/1.12 (29.5) | 3.47 (1.83, 6.59) | | 2.91 (1.41, 6.00) | |
| 60+ | 25/193 (13.0) | 1 | | 1 | |
| Breslow depth (mm) | | | <0.001 | | 0.036 |
| 0.50-1 | 6/93 (6.4) | 1 | | 1 | |
| 1.01-2 | 31/177 (17.5) | 3.33 (1.31, 8.44) | | 1.50 (0.54, 4.21) | |
| 2.01-4 | 37/90 (41.1) | 11.46 (4.34, 30.27) | | 3.30 (1.11, 9.77) | |
| Ulceration | | | 0.026 | | 0.39 |
| No | 50/295 (16.9) | 1 | | 1 | |
| Yes | 24/65 (36.9) | 2.11 (1.10, 4.06) | | 1.38 (0.66, 2.88) | |
| ITLP gene expression† | | | | | <0.001 |
| Negative | 10/237 (4.2) | -- | | 1 | |
| Positive | 64/133 (52.0) | -- | | 17.32 (8.02, 37.41) | |
| Mitotic rate | | | | | |
| Absent | 4/42 (9.5) | -- | | -- | |
| 1-6 | 51/246 (20.7) | -- | | -- | |
| >6 | 15/58 (25.9) | -- | | -- | |

CI confidence interval; OR, odds ratio; SLN, sentinel lymph noode.
†ITLP gene expression was negative if: ITGB3 ≤ 10, TP53 > 50 and neither LAMB1 > 250 or PLAT > 427

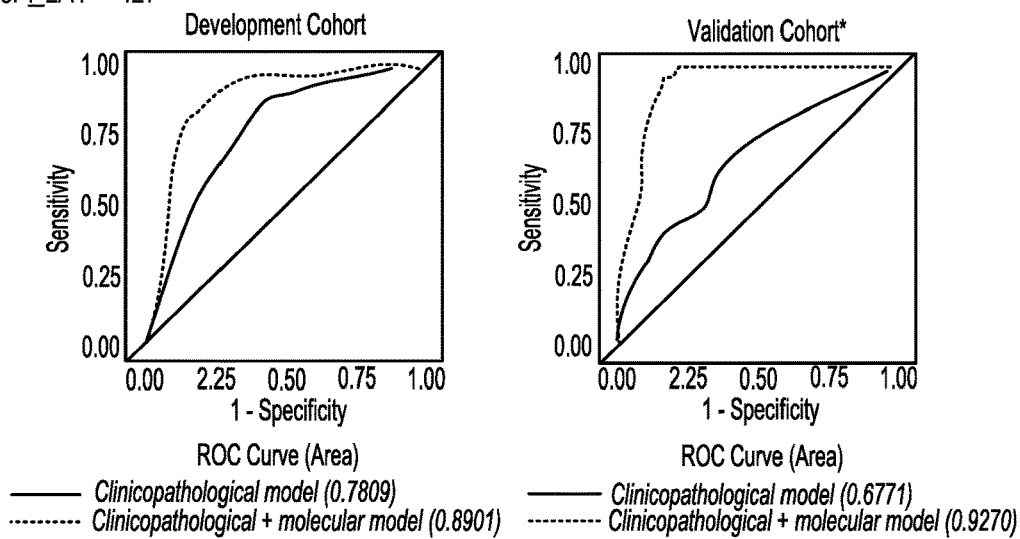

Development Cohort / Validation Cohort*

ROC Curve (Area)
—— Clinicopathological model (0.7809)
---------- Clinicopathological + molecular model (0.8901)

ROC Curve (Area)
—— Clinicopathological model (0.6771)
---------- Clinicopathological + molecular model (0.9270)

*False-positive and false-negative rates of 22% and 0%, respectively (validation cohort), using a 10% cutoff for predicted SLN metastasis risk).

METHODS AND MATERIALS FOR STAGING AND TREATING SKIN CANCER

CROSS-REFERENCE TO RELATED APPLICATIONS

This application is a National Stage application under 35 U.S.C. § 371 of International Application No. PCT/US2017/031908, having an International Filing Date of May 10, 2017, which claims priority to U.S. Application Ser. No. 62/334,302, filed on May 10, 2016. This disclosures of the prior applications are considered part of (and are incorporated by reference in) the disclosure of this application.

BACKGROUND

1. Technical Field

This document relates to methods and materials for staging and treating skin cancer (e.g., metastatic malignant pigmented skin lesions). For example, this document relates to methods and materials for using an ITLP expression profile and/or models including an ITLP expression profile to stage skin cancer and/or determine treatment options for skin cancer patients.

2. Background Information

Malignant skin lesions are typically identified by obtaining a skin biopsy and morphologically assessing the biopsy's melanocytes under a microscope. Such a procedure can be difficult to standardize and can lead to overcalling of melanomas. Once a diagnosis of melanoma is made by morphological assessment, the risk of metastasis is typically determined by the invasion depth of malignant cells into the skin (i.e., the Breslow depth). The Breslow depth can dictate further work-up such as a need for an invasive sentinel lymph node (SLN) procedure. Such procedures, however, can lead to inaccurate determinations of the true malignant potential of a pigmented lesion.

SUMMARY

This document provides methods and materials for staging and treating skin cancer (e.g., metastatic malignant pigmented skin lesions). For example, this document relates to methods and materials for using an ITLP expression profile and/or models including an ITLP expression profile to stage skin cancer.

As described herein, ITGB3, TP53, LAMB1, and PLAT expression levels (e.g., RNA copy numbers) can be determined for skin cancer cells of a mammal (e.g., a human with skin cancer such as melanoma) and used to classify the skin cancer as being ITLP negative or ITLP positive. In some cases, a skin cancer (e.g., melanoma) can be classified as being ITLP negative if the expression levels for that particular skin cancer are such that the RNA copy numbers are as follows: ITGB is ≤10, TP53 is >50, and neither LAMB1 is >250 nor PLAT is >427. If the expression levels for a skin cancer are such that the RNA copy numbers do not meet those conditions (i.e., do not meet the ITGB is ≤10, TP53 is >50, and neither LAMB1 is >250 nor PLAT is >427 conditions), then the skin cancer can be classified as being ITLP positive.

Quantitative PCR can be performed using a skin biopsy sample (e.g., a paraffin-embedded tissue biopsy) to obtain expression data (e.g., gene copy numbers) for one or more marker genes (e.g., ITGB3, TP53, LAMB1, and PLAT). Correction protocols can be used to reduce the impact of basal keratinocyte contamination on the analysis of the expression data from the test sample. For example, the contribution of gene expression from basal keratinocytes present within the test skin sample can be determined and removed from the overall gene expression values to determine the final gene expression value for a particular gene as expressed from cells other than basal keratinocytes (e.g., melanocytes). An assessment of the final gene expression values, which include minimal, if any, contribution from basal keratinocytes, for a collection of marker genes can be used to determine the positive or negative status of an ITLP expression profile.

As also described herein, a skin cancer (e.g., a melanoma) staged using a current staging system such as the American Joint Committee on Cancer (AJCC) tumor-node-metastasis (TNM) staging system (see, e.g., Edge et al., Ann. Surg. Oncol., 17(6):1471-4 (2010)) can be re-staged based on the skin cancer being ITLP positive. For example, a skin cancer (e.g., a melanoma) staged using a TNM staging system as being a stage I skin cancer can be re-staged as being a stage II skin cancer if the skin cancer is determined to be ITLP positive. In such cases, the mammal (e.g., human) having a skin cancer (e.g., a melanoma) staged as being a stage I skin cancer using a TNM staging system, yet being ITLP positive as described herein, can be treated in a manner similar to the treatment normally performed for those having a stage II skin cancer using a TNM staging system. For example, a mammal (e.g., a human) having a stage I skin cancer using a TNM staging system that also is ITLP positive can undergo a sentinel lymph node biopsy procedure.

In addition, a skin cancer (e.g., a melanoma) staged using a TNM staging system as being a stage II skin cancer can be re-staged as being a stage III skin cancer if the skin cancer is determined to be ITLP positive. In such cases, the mammal (e.g., human) having a skin cancer (e.g., a melanoma) staged as being a stage II skin cancer using a TNM staging system, yet being ITLP positive as described herein, can be treated in a manner similar to the treatment normally performed for those having a stage III skin cancer using a TNM staging system. For example, a mammal (e.g., a human) having a stage II skin cancer using a TNM staging system that also is ITLP positive can undergo adjuvant therapy such as adjuvant immunotherapy using high-dose interferon alfa or other therapies normally used for stage III melanoma.

Skin cancers staged using a TNM staging system can remain as staged if the skin cancer is determined to be ITLP negative.

This document also provides methods and materials for treating skin cancer. For example, this document provides methods and materials for restaging a skin cancer (e.g., melanoma) of a mammal (e.g., a human) that is ITLP positive as described herein and treating that mammal's skin cancer based on the restaged stage.

In general, one aspect of this document features a method for treating a mammal having skin cancer. The method comprises, or consists essentially of, (a) determining a TNM stage of the skin cancer using a TNM staging system, (b) determining that the skin cancer is ITLP positive, and (c) treating the mammal using a cancer treatment for a stage one greater than the TNM stage. The mammal can be a human. The skin cancer can be pre-metastatic skin cancer. The skin cancer can be pre-metastatic melanoma.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 12 is a table of the two indicated cohorts.
FIG. 13 is a multivariable model of SLN+.

DETAILED DESCRIPTION

This document provides methods and materials for staging and treating skin cancer (e.g., metastatic malignant pigmented skin lesions). For example, this document relates to methods and materials for using an ITLP expression profile and/or models including an ITLP expression profile to stage skin cancer.

In some cases, ITGB3, TP53, LAMB1, or PLAT expression levels (e.g., RNA copy numbers) can be determined for skin cancer cells of a mammal (e.g., a human with skin cancer such as melanoma) and used individually or in combination to adjust the stage of a skin cancer as described herein.

Any appropriate method can be used to determine ITGB3, TP53, LAMB1, and/or PLAT expression levels in skin cancer cells. For example, the methods and materials described in International Patent Application Serial No. PCT/US2015/045065 can be used to determine ITGB3, TP53, LAMB1, and/or PLAT expression levels in skin cancer cells.

Figure 1:
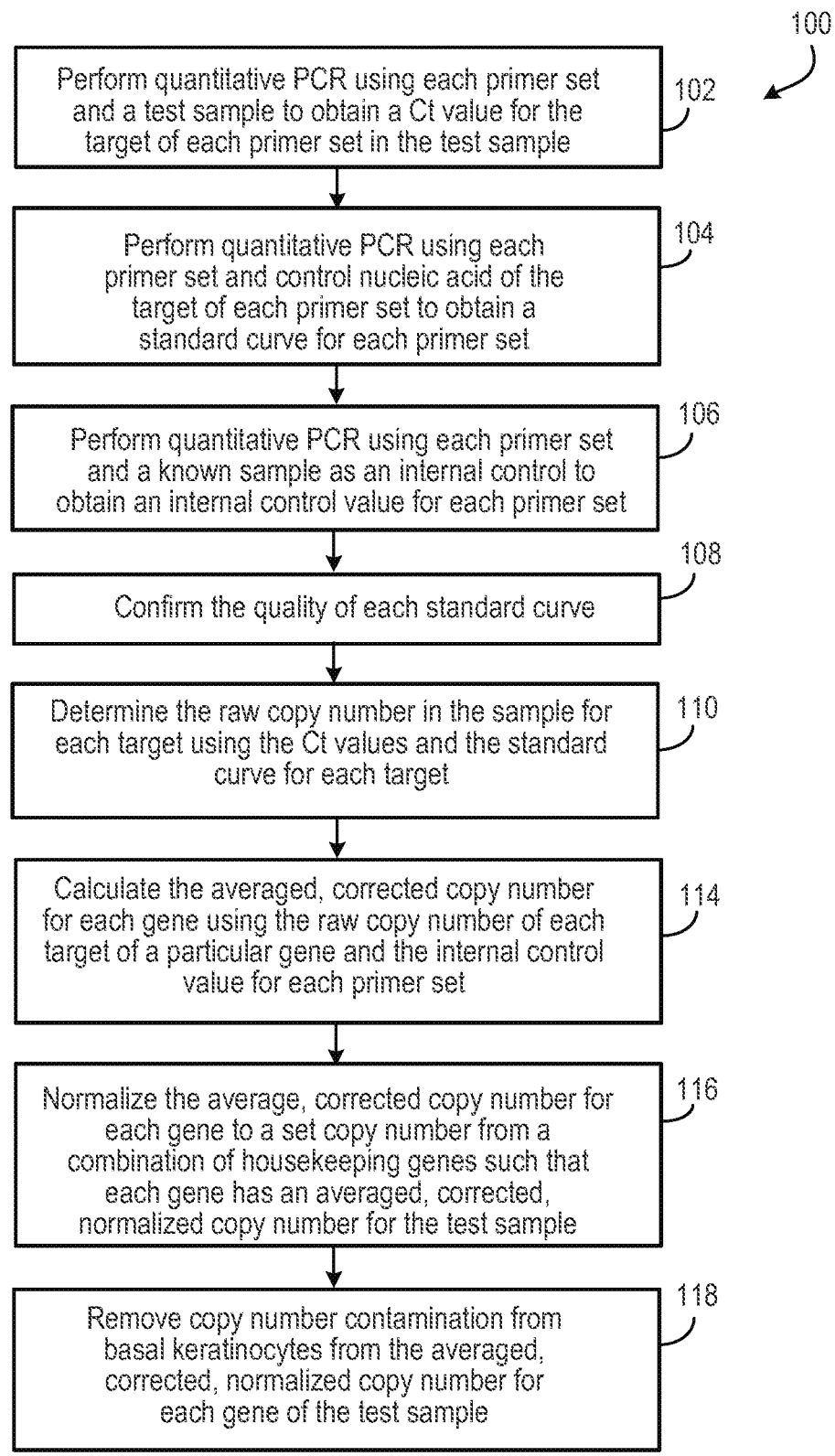
FIG. 1 is a flow chart of an exemplary process for determining the gene expression value, which includes minimal, if any, contribution from basal keratinocytes, for a marker gene by cells within a tested sample (e.g., a tested skin biopsy sample).

FIG. 1 shows an exemplary process 100 for determining a gene expression value, which includes minimal, if any, contribution from basal keratinocytes, for a marker gene by cells within a tested sample (e.g., a tested skin biopsy sample). The process begins at box 102, where quantitative PCR using a collection of primer sets and a test sample is used to obtain a Ct value for the target of each primer set. Each gene of interest can be assessed using a single primer set or multiple different primer sets (e.g., two, three, four, five, six, seven, or more different primer sets). In some cases, quantitative PCR is performed using each primer set and control nucleic acid of the target of each primer set (e.g., linearized cDNA fragments) to obtain a standard curve for each primer set as set forth in box 104. In some cases, quantitative PCR is performed using each primer set and a known sample as an internal control (e.g., a stock biological sample) to obtain an internal control value for each primer set as set forth in box 106. This internal control can be used to set values for each primer set across different assays. In some cases, the quantitative PCR performed according to boxes 102, 104, and 106 can be performed in parallel. For example, the quantitative PCR performed according to boxes 102, 104, and 106 can be performed in a single 96 well format.

At box 108, the quality of the obtained standard curves can be confirmed. In some cases, a gene of interest included in the assay format can be a melanocyte marker (e.g., levels of MLANA and/or MITF expression) to confirm the presence of melanocytes in the test sample. Other examples of melanocyte markers that can be used as described herein include, without limitation, TYR, TYRP1, DCT, PMEL, OCA2, MLPH, and MC1R.

At box 110, the raw copy number of each target present in the test sample is determined using the Ct values and the standard curve for each target. In some cases, the averaged, corrected copy number for each gene is calculated using the raw copy number of each target of a particular gene and the internal control value for each primer set (box 112). This averaged, corrected copy number value for each gene can be normalized to a set number of one or more housekeeping genes as set forth in box 114. For example, each averaged, corrected copy number value for each gene can be normalized to 100,000 copies of the combination of ACTB, RPL8, RPLP0, and B2M. Other examples of housekeeping genes that can be used as described herein include, without limitation, RRN18S, GAPDH, PGK1, PPIA, RPL13A, YWHAZ, SDHA, TFRC, ALAS1, GUSB, HMBS, HPRT1, TBP, CLTC, MRFAP1, PPP2CA, PSMA1, RPL13A, RPS29, SLC25A3, TXNL1, and TUPP. Once normalized, the copy number values for each gene can be referred to as the averaged, corrected, normalized copy number for that gene as present in the test sample.

At box 116, the averaged, corrected, normalized copy number for each gene can be adjusted to remove the copy number contamination from basal keratinocytes present in the test sample. In general, copy number contamination from basal keratinocytes can be removed by (a) determining a keratinocyte correction factor for the gene of interest using one or more keratinocyte markers (e.g., keratin 14 (K14)) and one or more normal skin samples (e.g., FFPE-embedded normal skin samples), (b) determining the averaged, corrected, normalized copy number value for the one or more keratinocyte markers of the test sample and multiplying that value by the keratinocyte correction factor to obtain a correction value for the gene of interest, and (c) subtracting that correction value from the averaged, corrected, normalized copy number value of the gene of interest to obtain the final copy number for the gene of interest. Examples of keratinocyte markers that can be used as described herein include, without limitation, KRT5, KRT1, KRT10, KRT17, ITGB4, ITGA6, PLEC, DST, and COL17A1.

Figure 2:
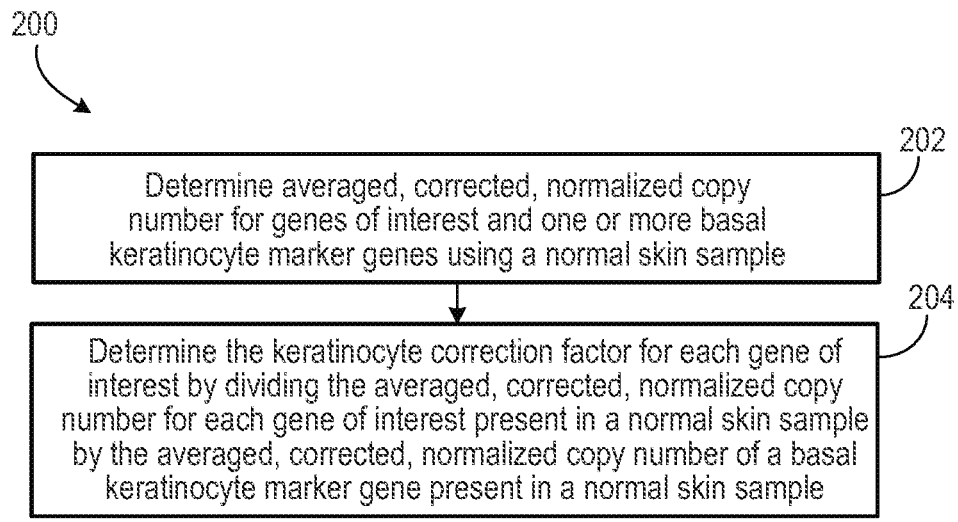
FIG. 2 is a flow chart of an exemplary process for determining a keratinocyte correction factor for a marker gene of interest.

With reference to FIG. 2, process 200 can be used to obtain a keratinocyte correction factor for a gene of interest. At box 202, the averaged, corrected, normalized copy number for one or more genes of interest (e.g., Gene X) and one or more basal keratinocyte marker genes (e.g., K14) are determined using one or more normal skin samples and procedures similar to those described in FIG. 1. As box 204, the keratinocyte correction factor for each gene of interest (e.g., Gene X) is determined by dividing the averaged, corrected, normalized copy number for each gene of interest present in a normal skin sample by the averaged, corrected, normalized copy number of a basal keratinocyte marker gene present in a normal skin sample. Examples of keratinocyte correction factors for particular genes of interest are set forth in Table E under column "AVG per copy K14."

Figure 3:
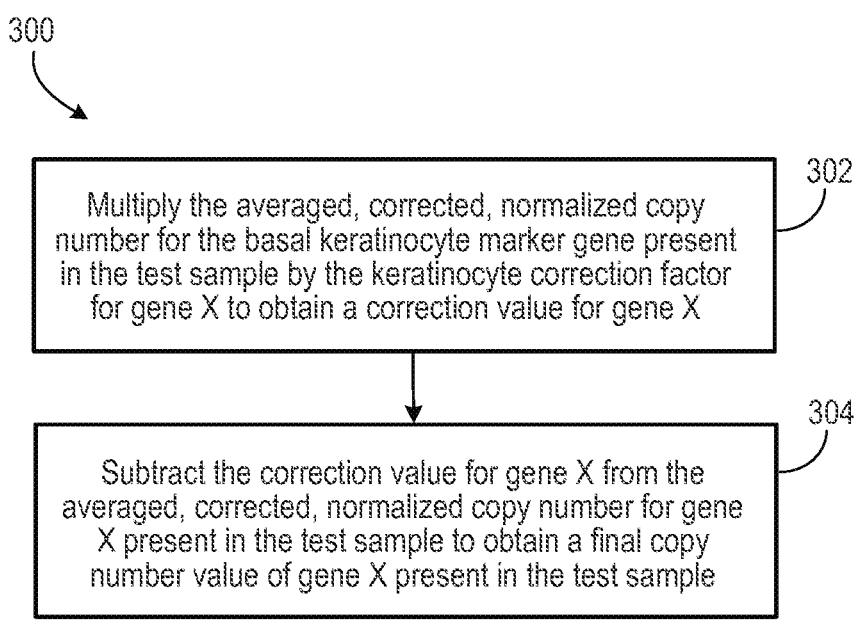
FIG. 3 is a flow chart of an exemplary process for removing copy number contamination from basal keratinocytes from a copy number value for a marker gene to determine the gene expression value, which includes minimal, if any, contribution from basal keratinocytes, for that marker gene by cells within a tested sample (e.g., a tested skin biopsy sample).

With reference to FIG. 3, once a keratinocyte correction factor in determined for a particular gene of interest (e.g., Gene X), then the averaged, corrected, normalized copy number for the basal keratinocyte marker gene present in the test sample can be multiplied by the keratinocyte correction factor for the gene of interest (e.g., Gene X) to obtain a correction value for the gene of interest (e.g., Gene X). See, e.g., box 302. At box 304, the correction value for the gene of interest (e.g., Gene X) is subtracted from the averaged, corrected, normalized copy number for the gene of interest (e.g., Gene X) present in the test sample to obtain a final copy number value of the gene of interest (e.g., Gene X) present in the test sample.

Figure 4:
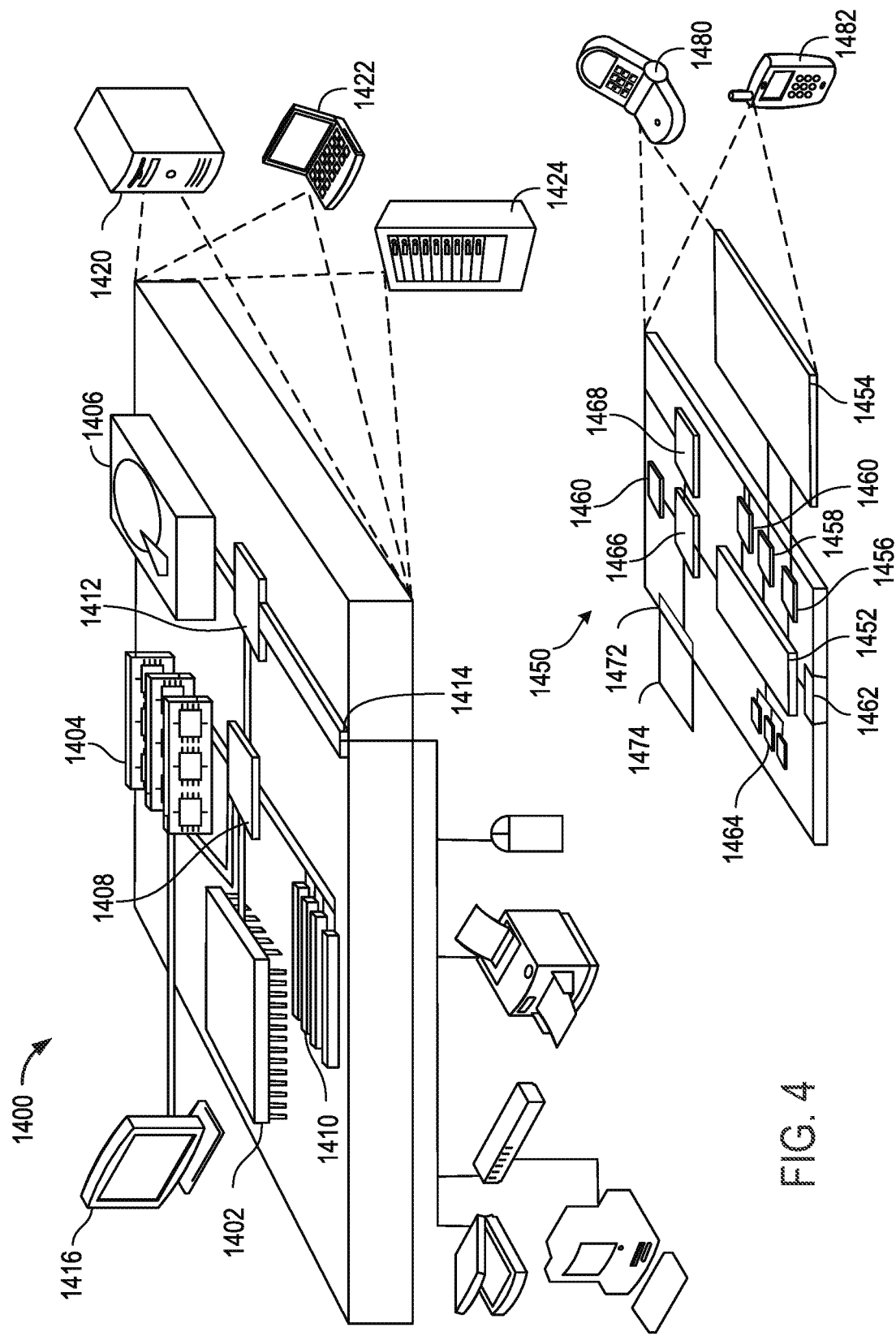
FIG. 4 is a diagram of an example of a generic computer device and a generic mobile computer device that can be used as described herein.

FIG. 4 is a diagram of an example of a generic computer device 1400 and a generic mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. In some cases, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

This document also provides methods and materials involved in treating mammals having skin cancer (e.g., melanoma such as pre-metastatic melanoma). Any appropriate mammal having skin cancer can be treated as described herein. For example, humans and other primates such as monkeys having skin cancer can be treated as described herein. In some cases, dogs, cats, horses, bovine species, porcine species, mice, or rats can be treated as described herein. In addition, a mammal having any particular type of skin cancer can be treated as described herein. For example, a mammal having melanoma, pre-metastatic melanoma, locally metastatic melanoma (i.e., skin in close proximity to primary melanoma), regionally metastatic melanoma (e.g., metastases to regional sentinel lymph nodes), or distant metastases (e.g., metastases to internal organs) can be treated as described herein. In some cases, a mammal (e.g., a human) determined to have skin cancer (e.g., a melanoma) staged using a TNM staging system as being a stage I skin cancer can be re-staged as being a stage II skin cancer if the skin cancer is determined to be ITLP positive. In such cases, the mammal (e.g., human) having a skin cancer (e.g., a melanoma) staged as being a stage I skin cancer using a TNM staging system, yet being ITLP positive as described herein, can be treated in a manner similar to the treatment normally performed for those having a stage II skin cancer using a TNM staging system. For example, a mammal (e.g., a human) having a stage I skin cancer using a TNM staging system that also is ITLP positive can undergo a sentinel lymph node biopsy procedure.

In some cases, a mammal (e.g., a human) determined to have a skin cancer (e.g., a melanoma) staged using a TNM staging system as being a stage II skin cancer can be re-staged as being a stage III skin cancer if the skin cancer is determined to be ITLP positive. In such cases, the mammal (e.g., human) having a skin cancer (e.g., a melanoma) staged as being a stage II skin cancer using a TNM staging system, yet being ITLP positive as described herein, can be treated in a manner similar to the treatment normally performed for those having a stage III skin cancer using a TNM staging system. For example, a mammal (e.g., a human) having a stage II skin cancer using a TNM staging system that also is ITLP positive can undergo adjuvant therapy such as adjuvant immunotherapy using high-dose interferon alfa or other therapies normally used for stage III melanoma.

The invention will be further described in the following examples, which do not limit the scope of the invention described in the claims.

EXAMPLES

Example 1—Re-Staging Melanoma

Study Sample

The following results were based on N=353 melanoma patients.

Results

The patient and tumor characteristics of these 353 patients are summarized in Table 1.

TABLE 1

| Patient and Tumor Characteristics. | |
|---|---|
| Characteristic | Overall (N = 353) |
| Male gender, n (%) | 220 (62.3%) |
| Age at primary (years), Mean (SD) | 59.7 (17.0) |
| Age at primary (years), n (%) | |
| 16-39 | 54 (15.3%) |
| 40-59 | 110 (31.2%) |
| 60+ | 189 (53.5%) |
| Breslow depth (mm) | |
| 0.50-1 | 89 (25.2%) |
| 1.01-2 | 176 (49.9%) |
| 2.01-4 | 88 (24.9%) |
| Location, n (%) | |
| Head/Neck | 60 (17.0%) |
| Truck/extremities | 250 (70.8%) |
| Acral | 43 (12.2%) |
| Ulceration, n (%) | 63 (17.9%) |
| Mitotic rate, n (%) | |
| Absent | 40/339 (11.8%) |
| 1-6 | 243/339 (71.7%) |
| >6 | 56/339 (16.5%) |
| Tumor invading lymphocytes, n (%) | 239/323 (74.0%) |
| Angiolymphatic invasion, n (%) | 16 (4.5%) |
| Histologic type, n (%) | |
| Superficial spreading | 176 (49.9%) |
| Nodular | 68 (19.3%) |
| Unclassifiable | 29 (8.2%) |
| Desmoplastic | 16 (4.5%) |

TABLE 1-continued

Patient and Tumor Characteristics.

| Characteristic | Overall (N = 353) |
|---|---|
| Lentigo maligna | 15 (4.2%) |
| Spindled | 13 (3.7%) |
| Acral lentiginous | 9 (2.5%) |
| Spitzoid | 4 (1.1%) |
| Nevoid | 3 (0.9%) |
| Dermal | 1 (0.3%) |
| Not documented | 19 (5.4%) |
| A260/280 Ratio, Median (IQR) | 1.88 (1.85, 1.91) |
| RNA concentration (ng/μl), Median (IQR) | 174 (102, 273) |
| Tissue age (days), Median (IQR) | 972 (329, 1825) |
| N classification based on SLN biopsy, n (%) | |
| N0 | 282 (79.9%) |
| N1 | 46 (13.0%) |
| N2 or N3 | 25 (7.1%) |

Of the 353 patients, 64 developed a relapse (local, regional, or distant metastases) at a median of 1.8 years (IQR, 0.9-3.0) following the primary diagnosis. Of the remaining 289 patients without a documented relapse, the median duration of relevant clinical follow-up was 3.1 years (IQR 1.1-5.2). When limiting the follow-up to within the first five years following the primary diagnosis, 59 patients developed a relapse within 5 years. For patients with follow-up >5 years, their follow-up was truncated at 5 years. The results herein were based on the follow-up within the first five years following the primary diagnosis.

Table 2 summarizes the results of evaluating each factor univariately for an association with relapse, based on fitting univariate Cox models. Associations were summarized using the adjusted hazard ratios (HR) and corresponding 95% CI's estimated from the model parameters.

TABLE 2

Summary of Factors Evaluated Univariately for an Association with Relapse.

| Factor | Based on considering each patient's full follow-up | | Based on restricting each patient's follow-up to within the first 5 years following the primary diagnosis | |
|---|---|---|---|---|
| | Unadjusted HR (95% CI) | P | Unadjusted HR (95% CI) | P |
| Age at primary | | .57 | | .45 |
| 16-39 | 0.91 (0.42, 1.98) | | 0.69 (0.29, 1.65) | |
| 40-59 | 1.28 (0.76, 2.18) | | 1.21 (0.70, 2.10) | |
| 60+ | 1.0 | | 1.0 | |
| Sex | | .66 | | .38 |
| Male | 1.0 | | 1.0 | |
| Female | 1.12 (0.68, 1.84) | | 1.26 (0.75, 2.10) | |
| Breslow depth, mm | | <.001 | | <.001 |
| 0.50-1 | 1.0 | | 1.0 | |
| 1.01-2 | 2.68 (1.11, 6.45) | | 3.06 (1.18, 7.94) | |
| 2.01-4 | 7.24 (3.00, 17.47) | | 7.70 (2.96, 20.02) | |
| Ulceration | | <.001 | | <.001 |
| No | 1.0 | | 1.0 | |
| Yes | 2.78 (1.62, 4.76) | | 3.15 (1.82, 5.45) | |
| Mitotic rate | | <.001 | | <.001 |
| Absent | 1.0 | | 1.0 | |
| 1-6 | 2.90 (0.70, 12.03) | | 2.69 (0.65, 11.21) | |
| >6 | 8.80 (2.07, 37.43) | | 8.51 (1.99, 36.28) | |
| N stage | | <.001 | | <.001 |
| N0 | 1.0 | | 1.0 | |
| N1 | 4.28 (2.45, 7.46) | | 3.75 (2.11, 6.66) | |
| N2 or N3 | 5.97 (2.73, 13.07) | | 5.75 (2.64, 12.56) | |
| ITLP gene expression | | <.001 | | <.001 |
| Negative | 1.0 | | 1.0 | |
| Positive | 4.15 (2.50, 6.90) | | 4.06 (2.40, 6.87) | |
| Tumor-invading lymphocytes | | .040 | | .073 |
| No | 1.0 | | 1.0 | |
| Yes | 0.57 (0.33, 0.97) | | 0.60 (0.34, 1.05) | |
| Angiolymphatic invasion | | .027 | | .063 |
| No | 1.0 | | 1.0 | |
| Yes | 2.58 (1.11, 5.99) | | 2.39 (0.95, 5.97) | |

Abbreviations: HR, hazard ratio; CI, confidence interval.
ITLP gene expression was negative if ITGB ≤ 10, TP53 > 50, and neither LAMB1 > 250 nor PLAT > 427.

Tables 3-5 summarize a few different options for multi-variable models. In Table 3, model A was the model identified using stepwise and backward variable selection methods considering only the clinicopathologic variables. In model B, ITLP gene expression was added. The models in Tables 4 and 5 were different variations depending on whether 'Breslow Depth' was applied or 'mitotic rate' was removed.

TABLE 3

Multivariable Cox Regression Analyses of Factors Associated with Relapse

| Factor | Multivariable Model A Adjusted HR (95% CI) | P | Multivariable Model B Adjusted HR (95% CI) | P | Multivariable Model C Adjusted HR (95% CI) | P |
|---|---|---|---|---|---|---|
| Breslow depth, mm | | | | | | |
| 0.50-1 | — | | — | | — | |
| 1.01-2 | — | | — | | — | |
| 2.01-4 | — | | — | | — | |
| Ulceration | | .029 | | .051 | | .063 |
| No | 1.0 | | 1.0 | | 1.0 | |
| Yes | 1.94 (1.07, 3.51) | | 1.81 (1.00, 3.29) | | 1.77 (0.97, 3.21) | |
| Mitotic rate | | .002 | | .002 | | <.001 |
| Absent | 1.0 | | 1.0 | | 1.0 | |
| 1-6 | 2.33 (0.55, 9.90) | | 1.99 (0.47, 8.47) | | 1.0 | |
| >6 | 6.36 (1.47, 27.43) | | 5.50 (1.27, 23.83) | | 2.93 (1.67, 5.14) | |
| N stage | | <.001 | | .12 | | .041 |
| N0 | 1.0 | | 1.0 | | 1.0 | |
| N1 | 3.22 (1.79, 5.81) | | 1.73 (0.82, 3.64) | | 1.0 | |
| N2 or N3 | 4.48 (1.98, 10.16) | | 2.55 (1.02, 6.39) | | 1.58 (1.02, 2.47) | |
| ITLP gene expression | | | | .017 | | .004 |
| Negative | — | | 1.0 | | 1.0 | |
| Positive | — | | 2.39 (1.17, 4.90) | | 2.62 (1.37, 5.02) | |
| | C-index = 0.742 | | C-index = 0.757 | | C-index = 0.732 | |

Abbreviations: HR, hazard ratio; CI, confidence interval.
ITLP gene expression was negative if ITGB ≤ 10, TP53 > 50, and neither LAMB1 > 250 nor PLAT > 427. Model A selected using both stepwise and backward variable selection methods considering just the clinicopathologic variables.
Model B, added ITLP gene expression.
Model C, collapsed some of the categories of the variables in Model B.

TABLE 4

Multivariable Cox Regression Analyses of Factors Associated with Relapse.

| Factor | Multivariable Model A Adjusted HR (95% CI) | P | Multivariable Model B Adjusted HR (95% CI) | P |
|---|---|---|---|---|
| Breslow depth, mm | | .12 | | .26 |
| 0.50-1 | 1.0 | | 1.0 | |
| 1.01-2 | 2.24 (0.85, 5.94) | | 2.02 (0.76, 5.38) | |
| 2.01-4 | 3.06 (1.05, 8.87) | | 2.47 (0.83, 7.34) | |
| Ulceration | | .032 | | .048 |
| No | 1.0 | | 1.0 | |
| Yes | 1.91 (1.06, 3.47) | | 1.82 (1.00, 3.31) | |
| Mitotic rate | | .048 | | .037 |
| Absent | 1.0 | | 1.0 | |
| 1-6 | 2.36 (0.56, 10.00) | | 2.04 (0.48, 8.69) | |
| >6 | 4.91 (1.11, 21.64) | | 4.59 (1.03, 20.37) | |
| N stage | | .002 | | .17 |
| N0 | 1.0 | | 1.0 | |
| N1 | 2.62 (1.42, 4.86) | | 1.67 (0.80, 3.50) | |
| N2 or N3 | 3.40 (1.45, 7.98) | | 2.32 (0.92, 5.82) | |
| ITLP gene expression | | | | .058 |
| Negative | — | | 1.0 | |
| Positive | — | | 2.03 (0.98, 4.24) | |
| | C-index = 0.768 | | C-index = 0.775 | |

Abbreviations: HR, hazard ratio; CI, confidence interval.
ITLP gene expression was negative if ITGB ≤ 10, TP53 > 50, and neither LAMB1 > 250 nor PLAT > 427.
Model A, selected using both stepwise and backward variable selection methods considering just the clinicopathologic variables; after forcing in Breslow depth.
Model B, added ITLP gene expression.

TABLE 5

Multivariable Cox Regression Analyses of Factors Associated with Relapse.

| Factor | Multivariable Model A Adjusted HR (95% CI) | P | Multivariable Model B Adjusted HR (95% CI) | P |
|---|---|---|---|---|
| Breslow depth, mm | | .009 | | .027 |
| 0.50-1 | 1.0 | | 1.0 | |
| 1.01-2 | 2.59 (0.99, 6.79) | | 2.34 (0.89, 6.18) | |
| 2.01-4 | 4.52 (1.66, 12.32) | | 3.81 (1.37, 10.56) | |
| Ulceration | | .008 | | .012 |
| No | 1.0 | | 1.0 | |
| Yes | 2.17 (1.22, 3.84) | | 2.08 (1.18, 3.69) | |
| Mitotic rate | | | | |
| Absent | — | | — | |
| 1-6 | — | | — | |
| >6 | — | | — | |
| N stage | | .004 | | .19 |
| N0 | 1.0 | | 1.0 | |
| N1 | 2.46 (1.35, 4.52) | | 1.63 (0.79, 3.36) | |
| N2 or N3 | 2.92 (1.26, 6.74) | | 2.16 (0.89, 5.22) | |
| ITLP gene expression | | | | .070 |
| Negative | — | | 1.0 | |
| Positive | — | | 1.90 (0.95, 3.81) | |
| | C-index = 0.746 | | C-index = 0.751 | |

Abbreviations: HR, hazard ratio; CI, confidence interval.
ITLP gene expression was negative if ITGB ≤ 10, TP53 > 50, and neither LAMB1 > 250 nor PLAT > 427.
Model A, selected using both stepwise and backward variable selection methods considering just the clinicopathologic variables, but not mitotic rate.
Model B, added ITLP gene expression.

The c-index was an overall measure of the predictive ability of a model. In each set of models, the c-index increased when ITLP gene expression was added, although not substantially. The c-index values for the models in Table 4 were slightly higher. Also, the models were slightly overfit using the rule of thumb of 10 events per every factor degree of freedom.

Figure 5:
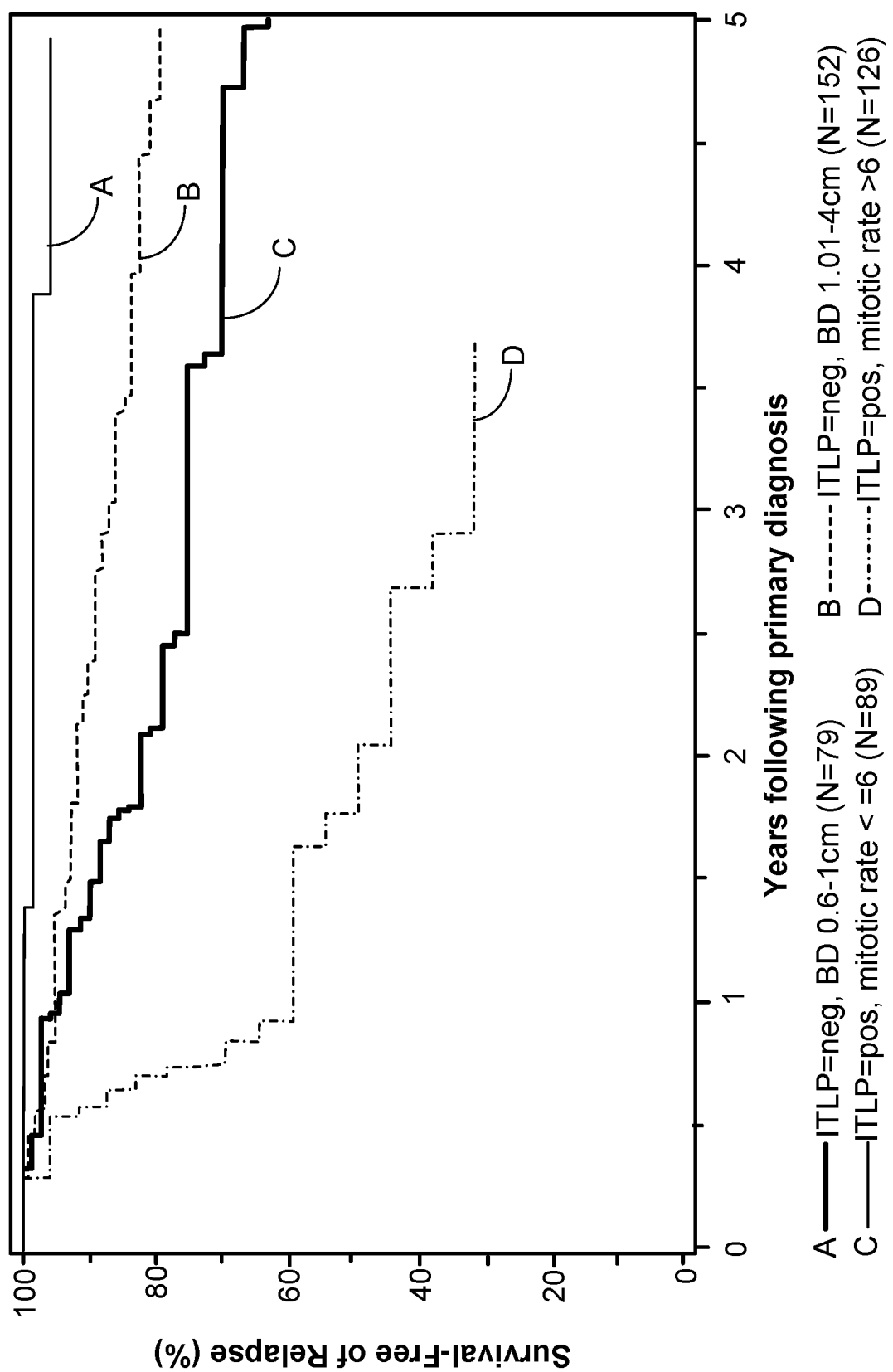
FIG. 5. The following variables were considered in the recursive partitioning: (a) Ulceration (presence/absence), (b) Breslow depth (<=1, 1.01-2, 2.01-4 cm), (c) N stage (N0, N1, N2 or N3), (d) mitotic rate (0, 1-6, >6), and ITLP gene expression (positive/negative). Within the subset of patients with a negative ITLP gene expression, they were further divided based on their Breslow depth. Within the subset of patients with a positive ITLP gene expression, they were further divided based on their mitotic rate. The results were based on 346 of the 353 patients (7 patients with a positive ITLP gene expression and unknown mitotic rate were excluded).
Figure 6:
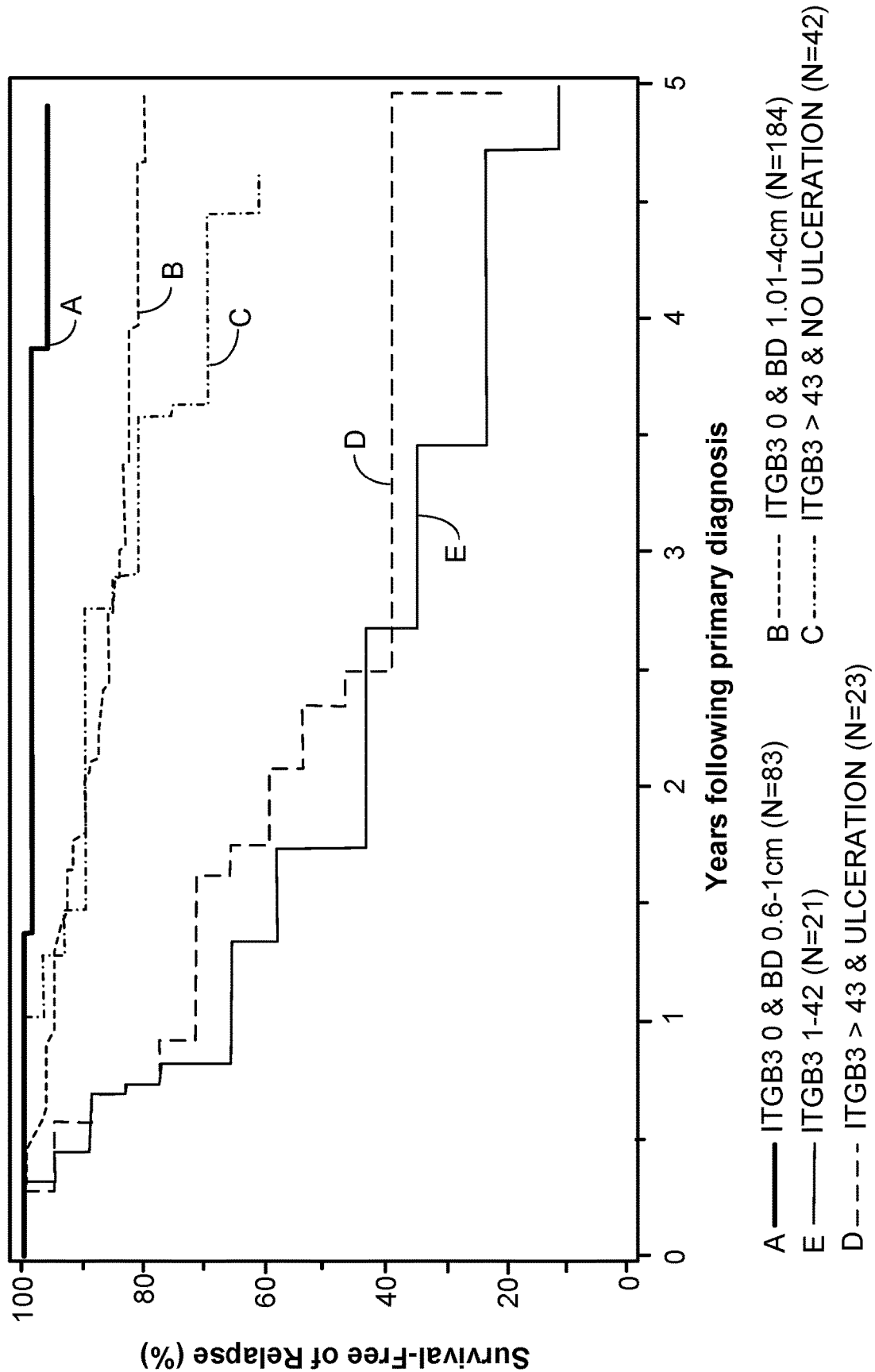
FIG. 6. The following variables were considered in the recursive partitioning: (a) Ulceration (presence/absence), (b) Breslow depth (<=1, 1.01-2, 2.01-4 cm), (c) N stage (N0, N1, N2 or N3), (d) mitotic rate (0, 1-6, >6), (e) ITGB3, (f) TP53, (g) LAMB1, and (h) PLAT. The presence of ulceration was a prognostic factor among those with ITGB3>43.
Figure 7:
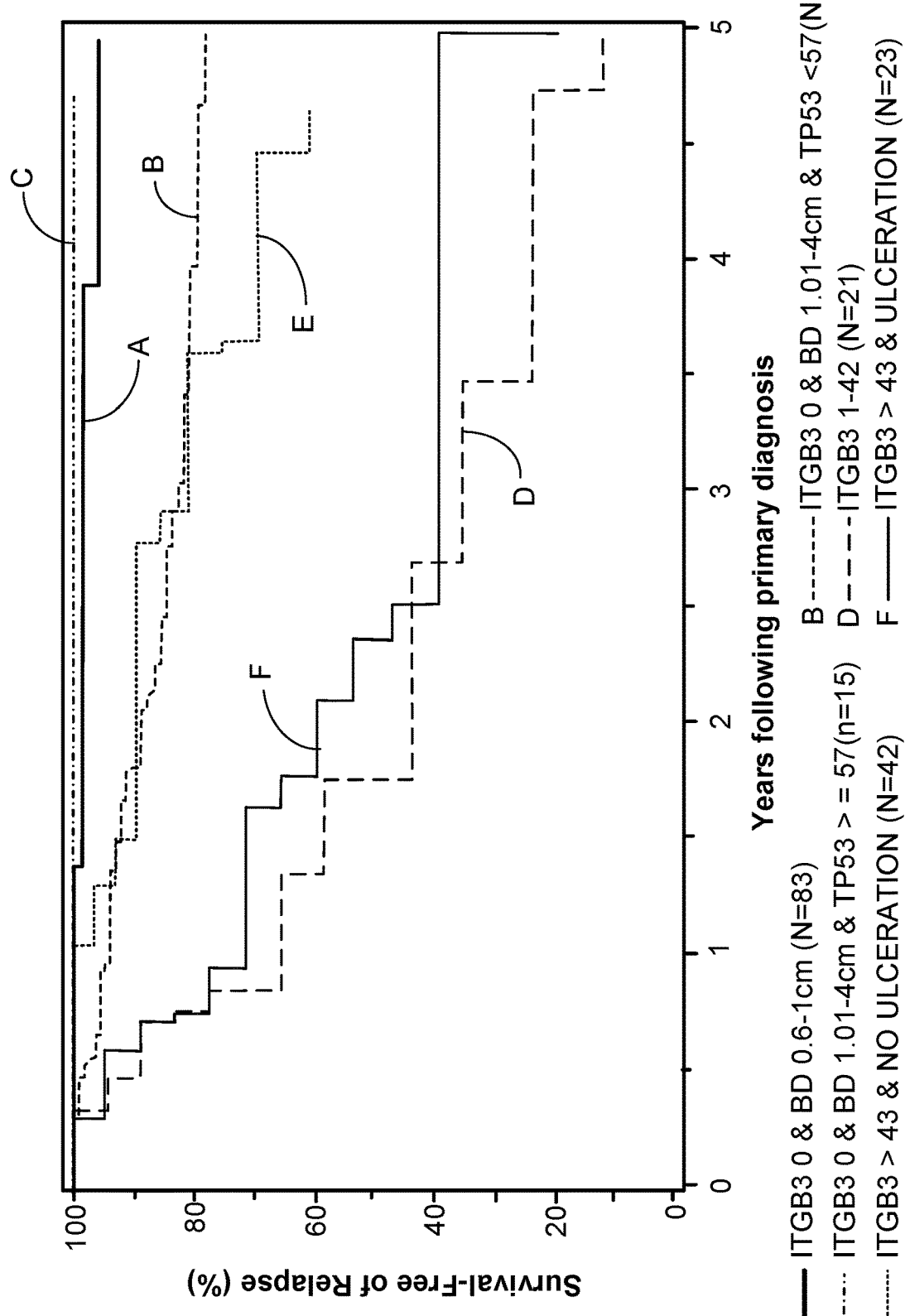
FIG. 7. The 184 patients in the subset denoted as having 184 patients in FIG. 6 was further subdivided into two subsets based on TP53<57 vs. ≥57.
Figure 8:
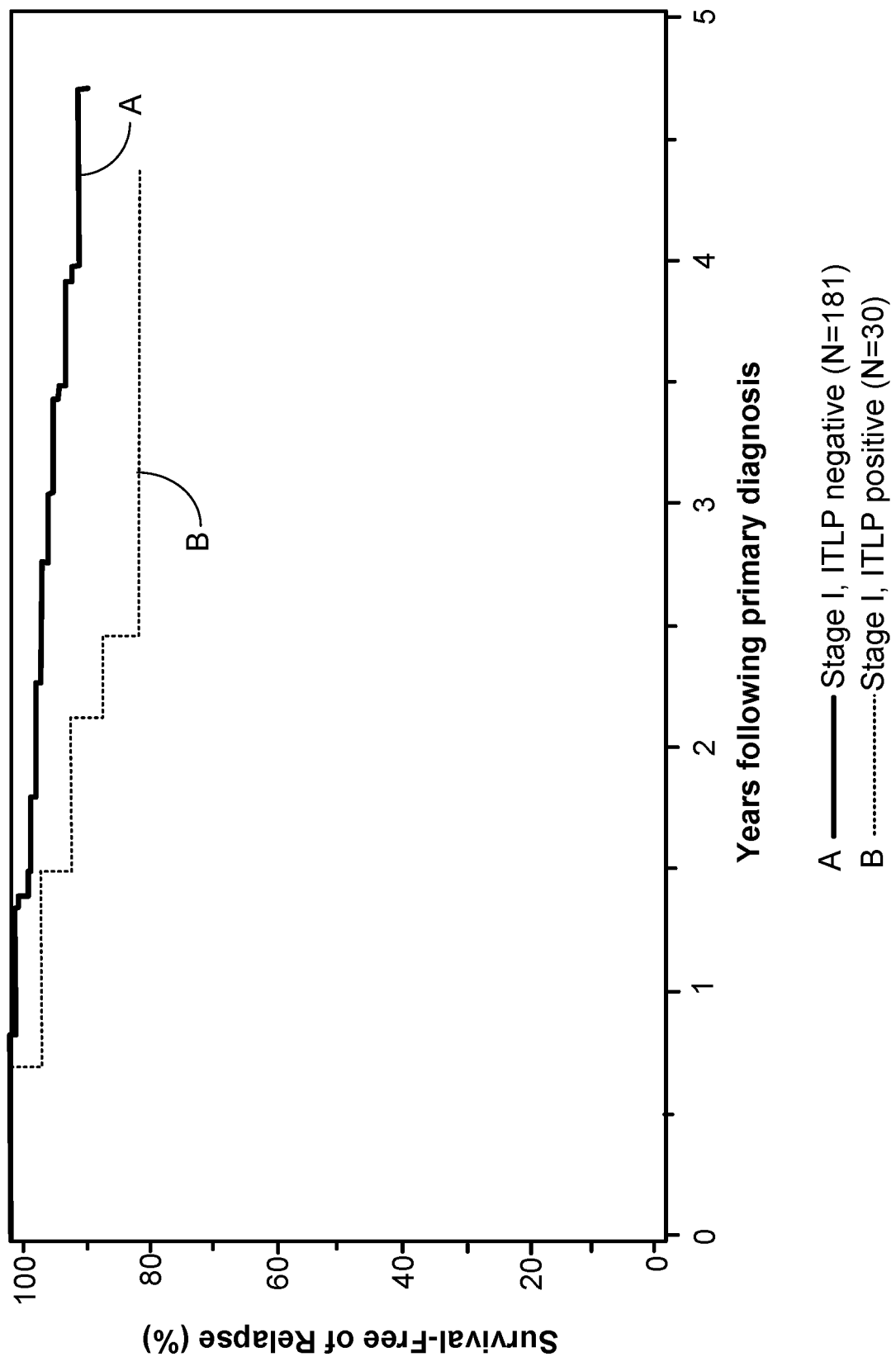
FIG. 8 is a graph plotting survival, free of relapse for originally staged Stage I, ITLP negative and ITLP positive patients.

A recursive partitioning (rpart package in R) was used in an exploratory analysis to identify subgroups of patients with different relapse profiles, based on presence/absence of ulceration, Breslow depth categories, N stage, mitotic rate, and either the ITLP positive/negative marker or the levels of ITGB3, TP53, LAMB1, and PLAT. The profiles were depicted in FIG. 5-7.

Figure 9:
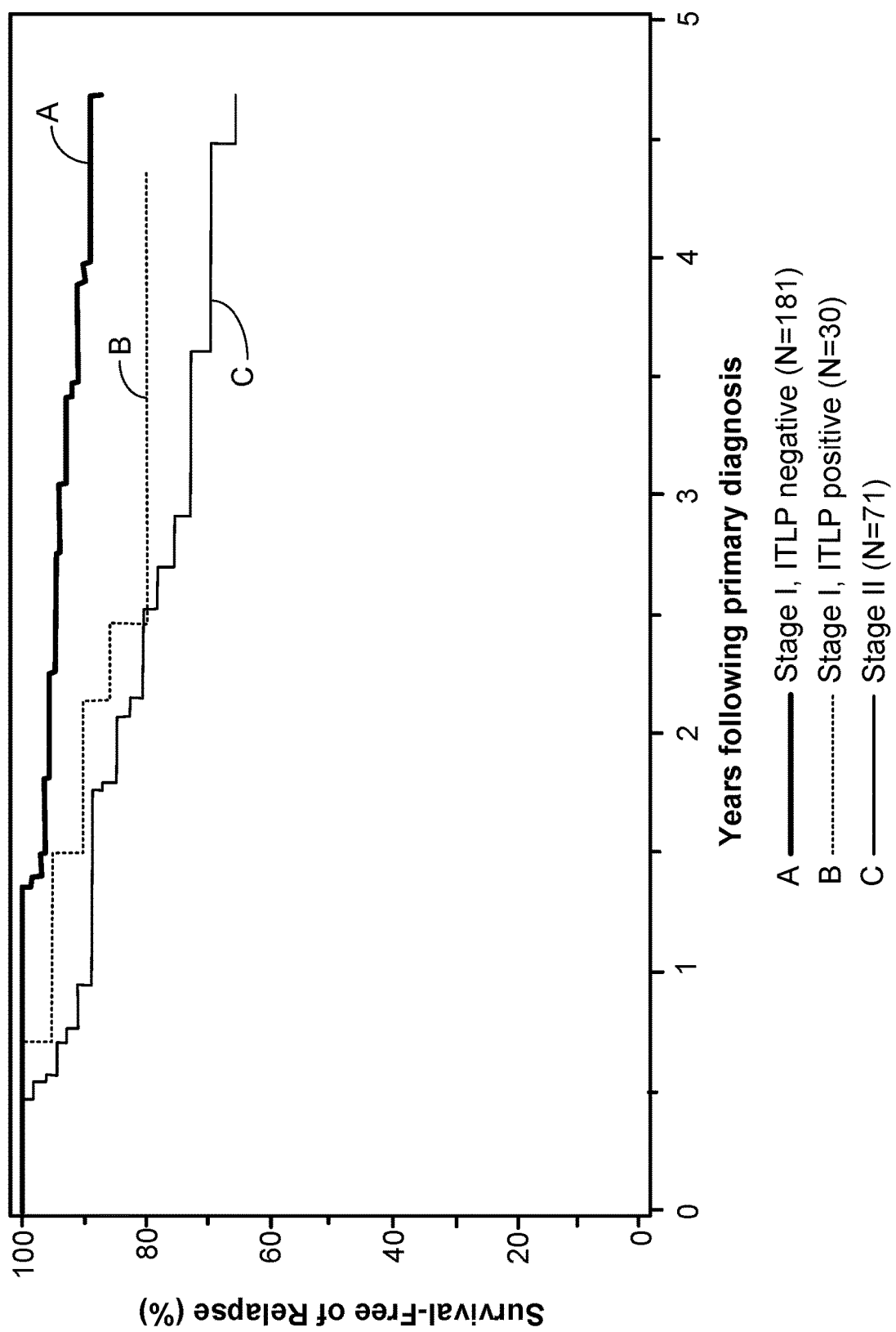
FIG. 9 is a graph plotting survival, free of relapse for originally staged Stage I, ITLP negative and ITLP positive patients as well as originally staged Stage II patients.
Figure 10:
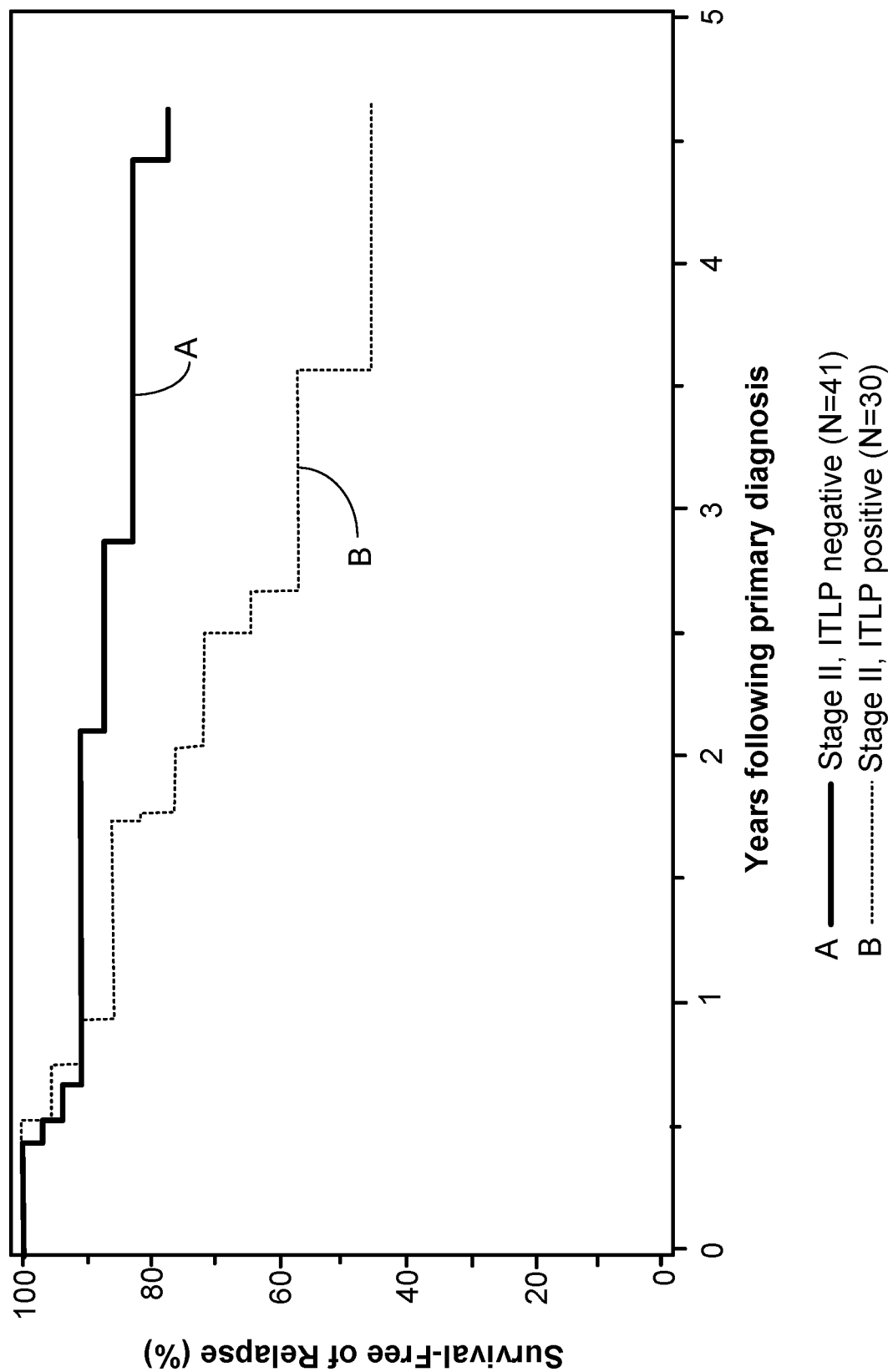
FIG. 10 is a graph plotting survival, free of relapse for originally staged Stage II, ITLP negative and ITLP positive patients.
Figure 11:
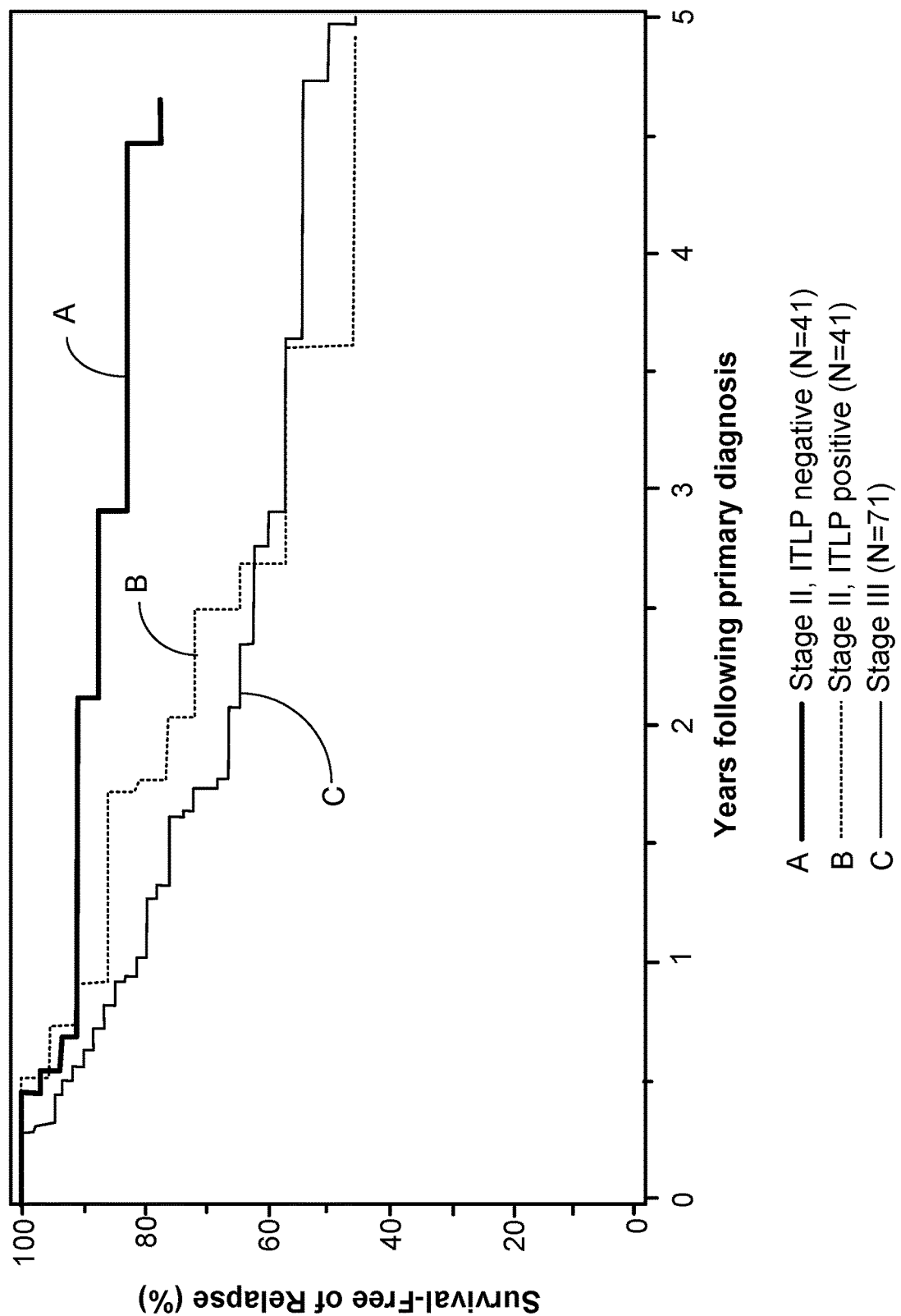
FIG. 11 is a graph plotting survival, free of relapse for originally staged Stage II, ITLP negative and ITLP positive patients as well as originally staged Stage III patients.

The results also were analyzed to determine the impact of positive ITLP on the original stage determinations based on survival, free of relapse data. Melanomas that were ITLP positive exhibited relapse likelihoods more in line with a one stage increase from their original stage determinations (FIGS. 9-11).

Example 2—Tumor Cell Adhesion as a Risk Factor for SLN Metastasis and Predictor of Disease Recurrence in Primary Cutaneous Melanoma Gene clusters with functional roles in melanoma metastasis were discovered by next generation sequencing and validated by quantitative PCR. PCR was used to quantify gene expression in a model development cohort of 360 consecutive thin and intermediate thickness melanomas and a validation cohort of 146 melanomas.

Outcomes of interest were: (i) SLN biopsy metastasis within 90 days of melanoma diagnosis, and (ii) melanoma recurrence after an initial workup period of 90 days.

Logic and logistic regression analyses were used to develop a model for the likelihood of SLN metastasis from molecular, clinical, and histologic variables. The molecular model was subsequently tested for its ability to predict melanoma recurrence.

Results

Figure 14:
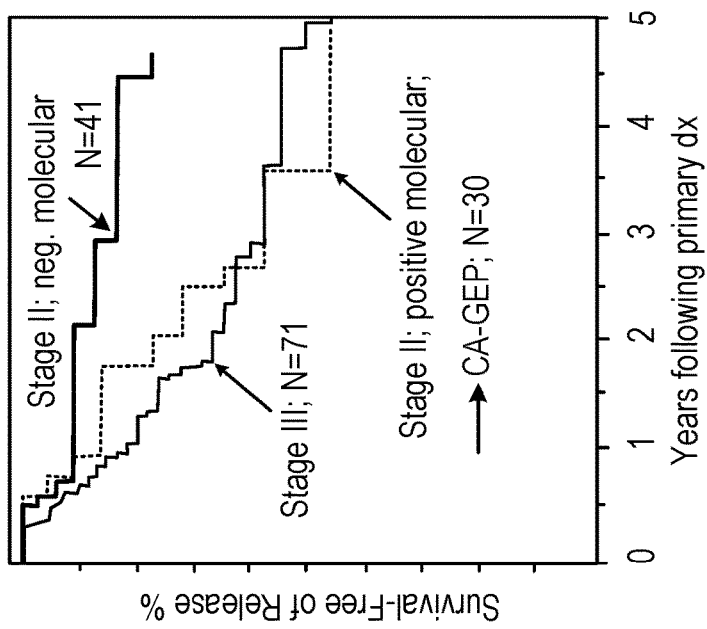
FIG. 14 is a multivariable model of relapse.

The predictive ability of models that included molecular information (cell adhesion) in combination with established clinicopathologic variables were significantly greater than models that only considered clinicopathologic variables. For predicting SLN metastasis, the false positive and false negative rates were 22% and 0%, respectively, using a 10% cutoff for predicted SLN metastasis risk. These results demonstrate a potential to eliminate >75% unnecessary SLNB. For melanoma relapse, a positive ITLP (cell adhesion remodeling) PCR signature significantly increased the risk of relapse by approximately +1 clinical stage. These results demonstrate that clinicians and patients should consider SLNB for stage I melanoma that is ITLP positive and should consider adjuvant therapy for stage II melanoma that is ITLP positive (FIGS. 12-14).

Example 3—Additional Validation of a Model for the Likelihood of SLN Metastasis from Molecular, Clinical, and Histologic Variables Table 6 contrasts the characteristics between the model development cohort and a model validation cohort. The two cohorts were similar with the exception that a higher proportion of patients in the model validation cohort had mitotic rate absent.

TABLE 6

| Characteristic | Model development cohort (N = 360) | Model validation cohort (N = 418) |
| --- | --- | --- |
| Male gender, n (%) | 225 (62.5%) | 256 (61.2%) |
| Age at SLN (years), Mean (SD) | 59.6 (17.0) | 60.2 (14.8) |
| Age at SLN (years), n (%) | | |
| 16-39 | 55 (15.3%) | 45 (10.8%) |
| 40-59 | 112 (31.1%) | 138 (33.0%) |
| 60+ | 193 (53.6%) | 235 (56.2%) |
| Breslow depth (mm) | | |
| 0.50-1 | 93 (25.8%) | 102 (24.4%) |
| 1.01-2 | 177 (49.2%) | 210 (50.2%) |
| 2.01-4 | 90 (25.0%) | 106 (25.4%) |
| Ulceration, n (%) | 65 (18.1%) | 98 (23.4%) |
| Mitotic rate, n (%) | | |
| Absent | 42/346 (12.1%) | 78/404 (19.3%) |
| 1-6 | 246/346 (71.1%) | 272/404 (67.3%) |
| >6 | 58/346 (16.8%) | 54/404 (13.4%) |
| SLN metastasis, n (%) | 74 (20.6%) | 76 (18.2%) |
| Positive ITLP gene expression, n (%) | 123 (34.2%) | 131 (31.3%) |

The overall discriminatory ability of the original model including both clinicopathologic factors (age category, Breslow depth, and ulceration) and the molecular factors (ITPL gene expression) in the model development cohort was 0.89 (95% CI 0.85-0.93). The discriminatory ability of the original model held up when applied to the validation cohort with an AUC of 0.87 (95% CI 0.83-0.91). Using the suggested cutoff of 10%, the false-positive rate in the validation cohort was 26.9% (92/342), and the false-negative rate was 7.9% (6/76).

These results demonstrate that the original model (Examples 1-2) validated well in this validation cohort.

What is claimed is:
1. A method for treating a mammal having a stage I TNM skin cancer, wherein said method comprises:
   (a) obtaining skin cancer cells from a mammal,
   (b) determining the mammal has stage I tumor-node-metastasis (TNM) skin cancer using the TNM staging system,
   (c) determining expression levels of ITGB3, TP53, LAMB1, and PLAT in the skin cancer cells obtained from the mammal having stage I TNM skin cancer,
   (d) detecting one of the following
      i) an RNA copy number for ITGB that is greater than 10,
      ii) an RNA copy number for TP53 that is less than 50,
      iii) an RNA copy number for LAMB that is less than 250, or
      iv) an RNA copy number for PLAT that is less than 427,
   (e) classifying the skin cancer as being ITLP-positive, and
   (f) treating the mammal having stage I TNM skin cancer with a sentinel lymph node biopsy.
2. The method of claim 1, wherein the mammal is a human.
3. A method for treating a mammal having a stage II TNM skin cancer, wherein said method comprises:
   (a) obtaining skin cancer cells from a mammal,
   (b) determining the mammal has stage II tumor-node-metastasis (TNM) skin cancer using the TNM staging system,
   (c) determining the expression levels of ITGB3, TP53, LAMB1, and PLAT in skin cancer cells obtained from the mammal having stage II TNM skin cancer, and

(d) detecting one of the following
   i) an RNA copy number for ITGB that is greater than 10,
   ii) an RNA copy number for TP53 that is less than 50,
   iii) an RNA copy number for LAMB that is less than 250, or
   iv) an RNA copy number for PLAT that is less than 427,
(e) classifying the skin cancer as being ITLP positive; and
(f) treating the mammal having stage II TNM skin cancer with adjuvant immunotherapy.

4. The method of claim 3, wherein the adjuvant immunotherapy is high-dose interferon alpha.

5. The method of claim 4, wherein the mammal is a human.

6. The method of claim 3, wherein the mammal is a human.

* * * * *